(12) United States Patent
Bristow

(10) Patent No.: US 9,801,381 B2
(45) Date of Patent: Oct. 31, 2017

(54) FORM OF RIMSULFURON, A PROCESS FOR ITS PREPARATION AND USE OF THE SAME

(71) Applicant: ROTAM AGROCHEM INTERNATIONAL COMPANY LIMITED, Chai Wan (HK)

(72) Inventor: James Timothy Bristow, Chai Wan (HK)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 36 days.

(21) Appl. No.: 15/081,362

(22) Filed: Mar. 25, 2016

(65) Prior Publication Data

US 2016/0286814 A1 Oct. 6, 2016

(30) Foreign Application Priority Data

Mar. 30, 2015 (GB) .................................. 1505464.6

(51) Int. Cl.
| | | |
|---|---|---|
| *C07D 401/12* | (2006.01) | |
| *A01N 47/36* | (2006.01) | |
| *A01N 25/12* | (2006.01) | |
| *A01N 25/14* | (2006.01) | |
| *A01N 41/10* | (2006.01) | |

(52) U.S. Cl.
CPC ............. *A01N 47/36* (2013.01); *A01N 41/10* (2013.01); *C07D 401/12* (2013.01)

(58) Field of Classification Search
CPC ............................... A01N 47/36; C07D 401/12
See application file for complete search history.

(56) References Cited

U.S. PATENT DOCUMENTS

| | | | | |
|---|---|---|---|---|
| 5,550,238 A | * | 8/1996 | Chiang ................ | C07D 521/00 544/206 |
| 2013/0252818 A1 | | 9/2013 | Lovejoy et al. | |
| 2015/0031877 A1 | * | 1/2015 | Hiratsuka ............. | A01N 43/84 544/105 |

FOREIGN PATENT DOCUMENTS

| | | |
|---|---|---|
| CN | 101671328 A | 3/2010 |
| EP | 341011 * | 11/1989 |
| WO | 2013143927 A1 | 10/2013 |

OTHER PUBLICATIONS

McClurg, R.B., "X-Ray Powder Diffraction (XRPD) to Describe Crystal Forms," Publication of SSCI an Aptuit Company, Jul. 9, 2008, pp. 1-23.*
HCAPLUS abstract 1999:261209 (1999).*
Roberts, R.M. et al. Modern Experimental Organic Chemistry. Holt, Rinehart and Winston, New York, 1979, pp. 49-58.*
International Search Report PCT/CN2016/077620 Mailed Jul. 4, 2016.
Written Opinion of PCT/CN2016/077620 Dated Jun. 15, 2016.
Tong, Jun et al. New Synthetic Method of Rimsulfuron. Chemical Intermediate Dec. 31, 2009 (Dec. 31, 2009) No. 5, pp. 29-31.
Tan, Xiaojun et al. Synthesis of Sulfonylurea Herbicide Rimsulfuron. Fine Chemical Intermediates Jun. 30, 2005 (Jun. 30, 2005) No. 3. vol. 35, pp. 26-27.
Zhang, Dayong et al. Synthesis of Rimsulfuron. Chinese Journal of Pesticides Dec. 31, 2005 (Dec. 31, 2005) No. 12 vol. 44, pp. 541-543.
Feng, Xiantong et al. Synthesis of Rimsulfuron. Agrochemicals Research & Applicatoin Jun. 30, 2006 (Jun. 30, 2006) No. 3 vol. 10, pp. 17-19.
Lu, Xinxin et al. Synthesis of Sulfonylurea Herbicide Rimsulfuron. Modem Agrochemicals Jun. 30, 2007 (Jun. 30, 2007), No. 3, vol. 6, pp. 13-15.

* cited by examiner

*Primary Examiner* — John Pak
(74) *Attorney, Agent, or Firm* — Dickinson Wright PLLC

(57) ABSTRACT

A crystal form of rimsulfuron is provided that exhibits improved solubility and decreased viscosity. Furthermore, a process for its preparation is provided. The novel crystal form is particularly suitable for use in herbicidal compositions and in the control of unwanted plant growth.

9 Claims, 3 Drawing Sheets

FORM OF RIMSULFURON, A PROCESS FOR ITS PREPARATION AND USE OF THE SAME

This US patent application claims benefit of UK patent application no. GB1505464.6, filed 30 Mar. 2015, the entire contents of which are incorporated herein by reference for all purposes.

FIELD OF THE INVENTION

The present invention relates to a crystal form of 1-(4,6-dimethoxypyrimidin-2-yl)-3-(3-ethylsulfonyl-2-pyridylsulfonyl)urea (rimsulfuron), to its preparation processes and to its use in agrochemical preparations.

DESCRIPTION OF RELATED ART 1-(4,6-dimethoxypyrimidin-2-yl)-3-(3-ethylsulfonyl-2-pyridylsulfonyhurea(rimsulfuron) is a potent herbicide having high selectivity, high efficiency, low toxicity and other desirable attributes. Rimsulfuron has a molecular formula of $C_{14}H_{17}N_5O_7S_2$. Its chemical structure is:

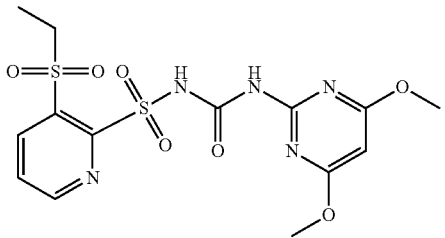 [SMILES: CCS(=O)(=O)c1cccnc1S(=O)(=O)NC(=O)Nc1nc(OC)cc(OC)n1]

It is used post-emergence on crops, such as maize and potatoes, against a variety of annual and perennial grasses and broadleaved weeds. It is rather less toxic towards algae and is of generally low toxicity towards most other wildlife.

The commercially available rimsulfuron, which is usually manufactured by the process described in EP0341011 A1, is present in an amorphous state. It has been found that rimsulfuron in amorphous state is highly viscous, which is not suitable for being prepared as compositions or formulations having spray equipment cleanout property. Rimsulfuron residues stay in the spray equipment after spraying. Adequate cleanout may require a rinsing procedure that is not only time-consuming but also results in wastewater disposal problems. Therefore, there is a need to provide a novel form of rimsulfuron with increased solubility and decreased viscosity.

SUMMARY

Accordingly the present invention provides a novel crystalline form of rimsulfuron, termed "crystal form A", and a process for its preparation as well as its use in agrochemical compositions. The novel crystalline form A has been advantageously found to have increased solubility, decreased viscosity and improved spray equipment clean-out properties. Accordingly, the invention also provides compositions for controlling undesirable plant growth, such as weeds, comprising the crystal form A of rimsulfuron on its own, as a mixture with auxiliaries and carriers, and as a mixture with other active compounds. The use of the crystal form A of rimsulfuron in the control of undesired plant growth and a method for the same are also provided by the present invention.

DETAILED DESCRIPTION OF EXAMPLE EMBODIMENTS

It has been found that the present crystal form A of rimsulfuron has a significant increase in its solubility and decrease in its viscosity, which significantly reduces the residue contamination and improve spray equipment cleanout properties. In addition, it has been found that the crystal form A of rimsulfuron is easier to be comminuted or ground compared to amorphous rimsulfuron prepared in accordance with the disclosure of EP0341011 A1. This allows the preparation of commercial formulations such as suspension concentrates (SC), oil-based suspension concentrates (OD), water-dispersible granules (WG) and water-soluble granules (SG). Hence, it is possible to prepare any formulations of rimsulfuron in crystal form A, which is disclosed hereinafter.

By virtue of its high solubility and low viscosity, the crystal form A of rimsulfuron is highly suitable for preparing compositions for controlling undesirable weeds.

According to a first aspect of the present invention a crystal form A of rimsulfuron is provided, exhibiting at least 3 of the following reflexes as 2θ values in an X-ray powder diffractogram recorded using Cu—Kα radiation at 25° C.:

| | |
|---|---|
| 2θ=10.868±0.2 | (1) |
| 2θ=12.248±0.2 | (2) |
| 2θ=12.845±0.2 | (3) |
| 2θ=14.249±0.2 | (4) |
| 2θ=15.039±0.2 | (5) |
| 2θ=16.120±0.2 | (6) |
| 2θ=17.434±0.2 | (7) |
| 2θ=18.010±0.2 | (8) |
| 2θ=19.699±0.2 | (9) |
| 2θ=21.801±0.2 | (10) |
| 2θ=22.568±0.2 | (11) |
| 2θ=26.567±0.2 | (12). |

Figure 1:
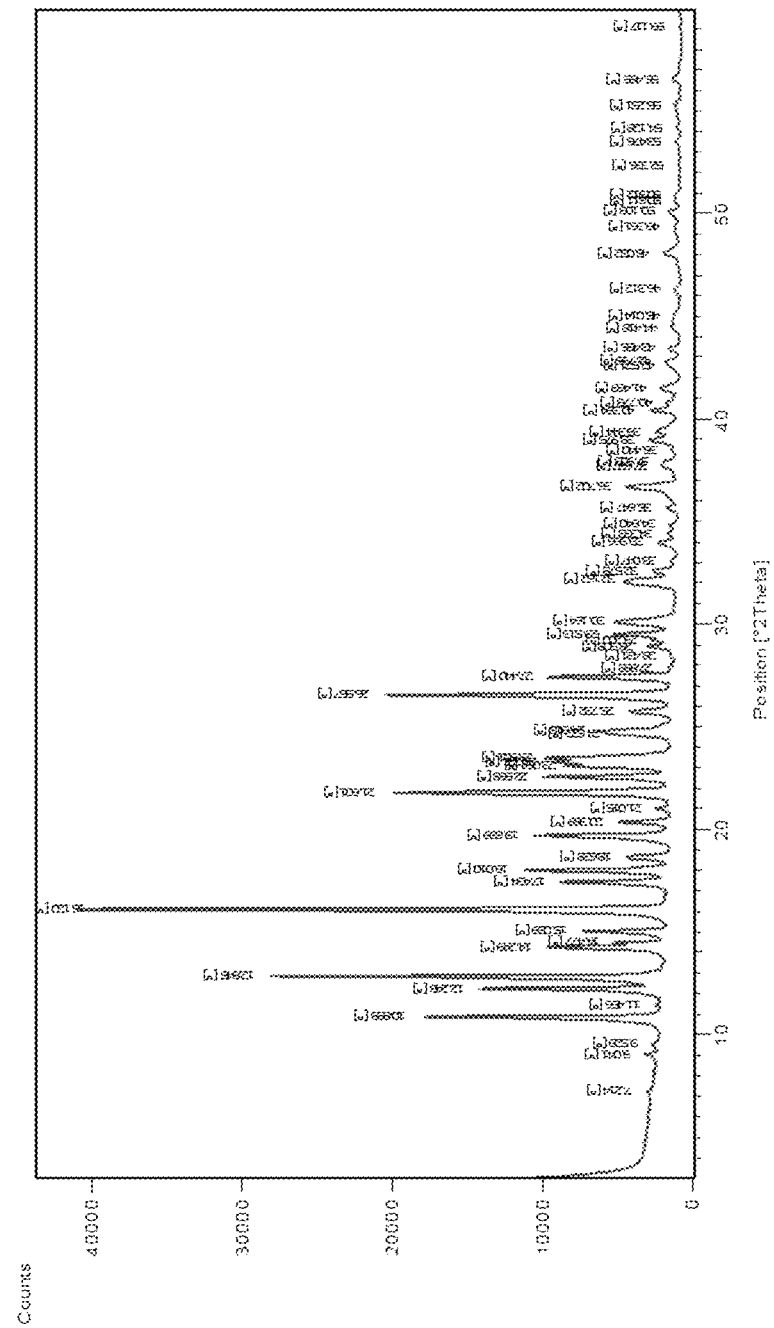
FIG. 1 is an X-ray powder diffractogram of a crystal form A of rimsulfuron.

The crystal form A of rimsulfuron of an embodiment of the present invention is characterized by an X-ray powder diffractogram having at least three of the reflexes indicated above. Preferably, the crystal form A is one having at least four of the aforementioned reflexes, more preferably at least five, six or seven, or eight of said reflexes. An X-ray powder diffractogram of the crystal form A of rimsulfuron is shown in FIG. 1, which will be described in detail hereinafter.

According to a preferred embodiment the crystalline form A exhibits at least 3, 4, or 5 or all of the reflexes from the following:

| | |
|---|---|
| 2θ=10.868±0.2 | (1) |
| 2θ=12.248±0.2 | (2) |
| 2θ=12.845±0.2 | (3) |

$$2\theta = 16.120 \pm 0.2 \quad (6)$$

$$2\theta = 21.801 \pm 0.2 \quad (10)$$

$$2\theta = 26.567 \pm 0.2 \quad (12)$$

Figure 2:
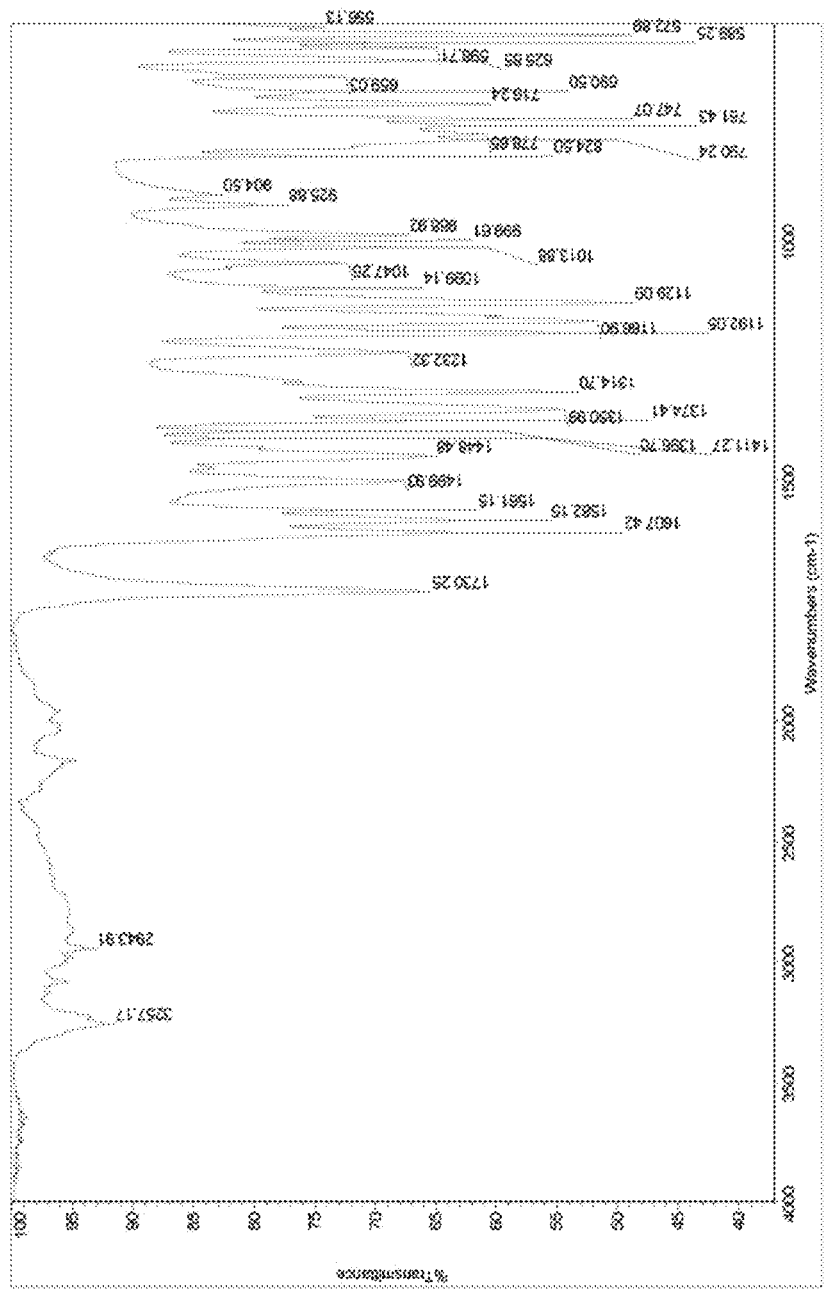
FIG. 2 is an IR spectrum of the crystal form A of rimsulfuron.

The crystal form A of rimsulfuron according to an embodiment of the present invention may be further characterized by Infrared (IR) spectroscopy. The IR spectrum of the crystal form A is shown in FIG. 2 with characteristic bands at 3257.17 cm$^{-1}$ and 2943.91 cm$^{-1}$.

All IR spectra were obtained using the following acquisition parameters:

| | |
|---|---|
| FT-IR spectrometer | Bruker Tensor37 |
| Diamond ATR unit | from Specac |
| Wavelength range | 550-4000 cm$^{-1}$ |
| Resolution | 4 cm$^{-1}$ |
| Number of scans | 16 |

Methods for preparing amorphous rimsulfuron are well known in the art. Amorphous rimsulfuron is manufactured and available on a commercial scale. A particularly suitable method for preparing amorphous rimsulfuron is described in EP0341011 A1.

According to an embodiment of the present invention, the crystal form A of rimsulfuron can be obtained by the processes below:

Rimsulfuron in an amorphous state is dissolved and then crystallized from a solvent.

In one aspect, the present invention provides a process for preparing a crystal form A of rimsulfuron comprising steps of:
  i) preparing a solution of an amorphous rimsulfuron in a solvent;
  ii) effecting crystallization of rimsulfuron from the solution to obtain a solid precipitate; and
  iii) isolating the solid precipitate.

Suitable solvents for preparing rimsulfuron crystal form A include halogenated hydrocarbons (for example, chlorobenzene, bromobenzene, dichlorobenzene, chlorotoluene and trichlorobenzene), ethers (for example, ethyl propyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyltetrahydrofuran, polyethers of ethylene oxide and/or propylene oxide), nitrated hydrocarbons (for example, nitromethane, nitroethane, nitropropane, nitrobenzene, chloronitrobenzene and o-nitrotoluene), aliphatic, cycloaliphatic or aromatic hydrocarbons (for example, pentane, n-hexane, n-heptane, n-octane, nonane), cymene, petroleum fractions within a boiling range of from 70° C. to 190° C., cyclohexane, methylcyclohexane, petroleum ether, ligroin, octane, benzene, toluene and xylene), esters (for example, malonates, acetic acid n-butyl ester (n-butyl acetate), methyl acetate, ethyl acetate, isobutyl acetate, dimethyl carbonate, diethyl carbonate, dibutyl carbonate and ethylene carbonate), and aliphatic alcohols (for example, methanol, ethanol, n-propanol, isopropanol, n-butanol and tert-amyl alcohol).

Preferred solvents are ethers, aromatic hydrocarbons (such as benzene, toluene, xylene, chlorobenzene), esters and aliphatic alcohols and mixtures thereof. Particularly preferred solvents or solvent mixtures are isopropanol, toluene, methyl-tetrahydrofuran, diethyl carbonate, chlorobenzene, n-butyl acetate, isobutyl acetate, n-butanol, ethanol, ethyl malonate, methyl t-butyl ether, and mixtures of toluene and butanol, toluene and n-butyl acetate, ethyl malonate and methyl t-butyl ether, as well as butyl acetate and methyl t-butyl ether. Solvent mixtures of more than 2 or 3 or 4 components are also envisaged by an embodiment of the present invention.

In an embodiment of the present invention, it is preferred that the solvent comprises at least one alcohol, more preferably comprises at least one straight or branched $C_1$-$C_8$ aliphatic alcohol, more preferably at least one straight or branched $C_1$-$C_4$ aliphatic alcohol, even more preferably methanol and ethanol.

According to another preferred embodiment the solvent essentially consists of an alcohol as mentioned above or mixtures thereof.

Hence, according to a preferred embodiment in step (i), amorphous rimsulfuron is dissolved in a solvent comprising an alcohol. In a preferred embodiment, the solvent essentially consists of methanol and/or ethanol.

In step (ii) of the process, rimsulfuron is crystallized from the solution. Techniques for effecting crystallization of rimsulfuron from the solution are known to those skilled in the art. For example, in an embodiment, where the solution in step (i) is formed at elevated temperatures, crystallization may be effected by cooling the solution to room or ambient temperature. In one preferred embodiment, crystallization is effected by concentrating the solution formed in step (i) of the process. Alternatively, or in addition thereto, seed crystals, in particular seed crystals of the aforementioned crystal form A of rimsulfuron, may be added to the solution formed in step (i), to facilitate and/or enhance crystallization.

It is preferred that the solid precipitate of rimsulfuron recovered during the crystallization stage is washed with a solvent one or more times. Preferably, the solvent employed in the washing stage consists of one or more components of the solvent employed for forming the solution in step (i), as described hereinbefore. Alcohols, preferably methanol and ethanol, are particularly suitable solvents for washing the recovered solid of rimsulfuron.

The invention also relates to a composition comprising the crystal form A of rimsulfuron. The amount of the crystal form A of rimsulfuron is less than 75% by weight of the composition, preferably less than 50% by weight of the composition, more preferably less than 30% by weight of the composition, still more preferably about 25% by weight of the composition.

The use of rimsulfuron as a herbicide is well known in the art and is used on a commercial scale. The crystal form A of rimsulfuron is also active in controlling unwanted plant growth, such as weeds. Techniques of formulating and applying rimsulfuron are known in the art, for example as disclosed in the prior art documents discussed hereinbefore. Rimsulfuron in the crystal form A of an embodiment of the present invention may be formulated and applied in an analogous manner.

Accordingly, in a further aspect, the present invention provides a herbicidal composition comprising rimsulfuron in the crystal form A as defined hereinbefore.

Accordingly, an embodiment of the present invention furthermore provides processes for preparing compositions for controlling unwanted plant growth using the crystal form A of rimsulfuron.

The crystal form A of rimsulfuron can be incorporated in a known manner to the customary formulations, such as suspension concentrates (SC), oil-based suspension concentrates (OD), water-soluble granules (SG), dispersible concentrates (DC), emulsifiable concentrates (EC), emulsion seed dressings, suspension seed dressings, granules (GR), microgranules (MG), suspoemulsions (SE) and water-dispersible granules (WG) using suitable auxiliaries, carriers and solvents.

In this context, the crystal form A of rimsulfuron may be present in a concentration of from about 0.1 to about 50% by weight of the total mixture, i.e., in amounts sufficient to achieve the required dosage. The formulations are prepared, for example, by extending the crystal form A of rimsulfuron with water, solvents and carriers, using, if appropriate, emulsifiers and/or dispersants, and/or other auxiliaries.

These formulations are prepared in a known manner by mixing the crystal form A of rimsulfuron with customary additives, for example, liquid diluents, solid diluents, wetting agents, dispersants, thickening agents and other formulation ingredients.

Liquid diluents include, but are not limited to, water, N,N-dimethylamide, dimethyl sulfoxide, N-alkylpyrrolidone, ethylene glycol, polypropylene glycol, propylene carbonate, dibasic esters, paraffines, alkylbenzenes, alkyl naphthalenes, glycerine, triacetin oils of olive, castor, linseed, sesame, corn, peanut, cotton-seed, soybean, rape-seed and coconut, ketones such as cyclohexanone, 2-heptanone, isophorone and 4-hydroxy-4-methyl-2-pentanone, acetates such as hexyl acetate, heptyl acetate and octyl acetate, and alcohols such methanol, cyclohexanol, decanol, benzyl and tetrahydrofurfuryl alcohol.

Solid diluents can be water-soluble or water-insoluble. Water-soluble solid diluents include, but are not limited to, salts such as alkali metal phosphates (e.g., sodium dihydrogen phosphate), alkaline earth phosphates, sulfates of sodium, potassium, magnesium and zinc, sodium and potassium chloride, sodium acetate, sodium carbonate and sodium benzoate, and sugars and sugar derivatives such as sorbitol, lactose, sucrose and mannitol. Examples of water-insoluble solid diluents include, but are not limited to clays, synthetic and diatomaceous silicas, calcium and magnesium silicates, titanium dioxide, aluminum, calcium and zinc oxide.

Wetting agents include, but are not limited to, alkyl sulfosuccinates, laureates, alkyl sulfates, phosphate esters, acetylenic diols, ethoxyfluornated alcohols, ethoxylated silicones, alkyl phenol ethyoxylates, benzene sulfonates, alkyl-substituted benzene sulfonates, alkyl a-olefin sulfonates, naphthalene sulfonates, alkyl-substituted napthalene sulfonates, condensates of naphthalene sulfonates and alkyl-substituted naphthalene sulfonates with formaldehyde, and alcohol ethoxylates. Alkyl naphthalene sulphonates, sodium salts are particularly useful for the composition of an embodiment of the invention Dispersants include, but are not limited to, sodium, calcium and ammonium salts of ligninsulfonates (optionally polyethoxylated); sodium and ammonium salts of maleic anhydride copolymers; sodium salts of condensed phenol-sulfonic acid; and naphthalene sulfonate-formaldehyde condensates. Of note are compositions comprising up to 10% by weight of dispersant. Ligninsulfonates such as sodium ligninsulfonates are particularly useful for the composition of an embodiment of the invention. Naphthalene sulfonate-formaldehyde condensates such as Naphthalenesulfonic acid, polymers with formaldehyde, and sodium salts are particularly useful for the composition of an embodiment of the invention Thickening agents include, but are not limited to, guar gum, pectin, casein, carrageenan, xanthan gum, alginates, methylcellulose, hydroxyethylcellulose, hydroxypropylcellulose, and carboxymethylcellulose. Synthetic thickeners include derivatives of the former categories, and also polyvinyl alcohols, polyacrylamides, polyvinylpyrrolidones, various polyethers, their copolymers as well as polyacrylic acids and their salts. Alkylpolyvinylpyrrolidones are particularly useful for the composition of an embodiment of the invention.

Other formulation ingredients can also be used in an embodiment of the present invention, such as dyes, defoamers, drying agents, and the like. These ingredients are known to one skilled in the art.

The crystal form A of rimsulfuron according to an embodiment of the invention can be present in formulations and in its use forms, prepared from these formulations, and as a mixture with other active compounds (such as insecticides, attractants, sterilizing agents, bactericides, acaricides, nematicides, fungicides, growth-regulating substances, herbicides, safeners, fertilizers and semiochemicals) or with agents for improving plant properties.

When used as a herbicide, the crystal form A of rimsulfuron according to an embodiment of the invention can furthermore be present in formulations and its use forms, prepared from these formulations, and as a mixture with inhibitors which reduce degradation of the active compounds after their use in the environment of the plant, on the surface of plant parts or in plant tissues.

All plants and plant parts can be treated in accordance with an embodiment of the present invention. In the present context, plants are to be understood as meaning all plants and plant populations such as desired and undesired wild plants or crop plants (including naturally occurring crop plants). Crop plants can be plants which can be obtained by conventional breeding and optimization methods, by biotechnological and genetic engineering methods, or by combinations of these methods, including the transgenic plants and the plant cultivars which can or cannot be protected by plant breeders' rights. Plant parts are to be understood as meaning all parts and organs of plants above and below the ground, such as shoot, leaves, needles, stalks, stems, flowers, fruit bodies, fruits, seeds, roots, tubers and rhizomes. Harvested materials, and vegetative and generative propagation materials, for example, cutting, tubers, meristem tissue, rhizomes, offsets, seeds, single and multiple plant cells and any other plant tissues, are also included.

As used herein, the term "about," when used in connection with a numerical amount or range, means somewhat more or somewhat less than the stated numerical amount or range, to a deviation of ±10% of the stated numerical amount or endpoint of the range.

"Surrounding," as used herein, refers to the place on which the plants are growing, the place on which the plant propagation materials of the plants are sown or the place on which the plant propagation materials of the plants will be sown.

Treatment according to examples of the present invention of the plants and plant parts with the compositions or formulations of examples of the inventions is carried out directly or by allowing the compositions or formulations to act on their surroundings, habitat or storage space by the customary treatment methods. Examples of these customary treatment methods include dipping, spraying, vaporizing, fogging, broadcasting, painting on in the case of propagation material, and applying one or more coats particularly in the case of seed.

The compositions or formulations of embodiments of the present invention may be used to control dicotyledonous weeds, such as *Abutilon* spp., *Ambrosia* spp., *Amaranthus* spp., *Chenopodium* spp., *Erysimum* spp., *Euphorbia* spp., *Fallopia* spp., *Galium* spp., *Hydrocotyle* spp., *Ipomoea* spp., *Lamium* spp., *Medicago* spp., *Oxalis* spp., *Plantago* spp., *Polygonum* spp., *Richardia* spp., *Sida* spp., *Sinapis* spp., *Solarium* spp., *Stellaria* spp., *Taraxacum* spp., *Trifolium* spp., *Veronica* spp., *Viola* spp. and *Xanthium* spp.

The compositions or formulations of embodiments of the present invention may also be used to control monocotyledonous weeds, such as *Agrostis* spp., *Alopecurus* spp., *Apera* spp., *Avena* spp., *Brachiaria* spp., *Bromus* spp., *Digitaria* spp., *Echinochloa* spp., *Eleusine* spp., *Eriochloa* spp., *Leptochloa* spp., *Lolium* spp., *Ottochloa* spp., *Panicum* spp., *Paspalum* spp., *Phalaris* spp., *Poa* spp., *Rottboellia* spp., *Setaria* spp., *Sorghum* spp., both intrinsically sensitive as well as resistant (e.g. ACCase and/or ALS resistant) biotypes of any of these grass weeds, as well as broadleaf monocotyledonous weeds such as *Commelina* spp., *Monochoria* spp., *Sagittaria* spp. and sedges such as *Cyperus* spp. and *Scirpus* spp.

The benefits of the present invention are seen most when the herbicidal composition is applied to kill weeds in growing crops of useful plants, such as maize (corn) including field corns, pop corns and sweet corns, cotton, wheat, rice, oats, potatoes, sugar beets, plantation crops (such as bananas, fruit trees, rubber trees, tree nurseries), vines, asparagus, bushberries (such as blueberries), caneberries, cranberries, flax, grain sorghum, okra, peppermint, rhubarb, spearmint and sugarcane. According to aspects of the present invention, maize and potatoes are more concerned.

Embodiments of the present invention will now be described by way of the following examples, which are provided for illustrative purposes only, and not intended to limit the scope of the disclosure.

All percentages are given in weight % unless otherwise indicated.

EXAMPLES

Example 1

Preparation of Amorphous Rimsulfuron in Accordance with the Disclosure of EP0341011 A1

To a stirred suspension of 0.60 g (0.0024 mol) of 3-ethylsulfonyl-2-pyridinesulfonamide and 0.90 g (0.0034 mol) of phenyl (4,6-dimethoxypyrimidin-2-yl)carbamate in 5 ml acetonitrile, 0.52 g (0.0034 mol) of 1,8-diazabicyclo[5.4.0]undec-7-ene (DBU) was added and stirred for 15 minutes. The solution was diluted with water and acidified with hydrochloric acid. The resulting solid precipitate was collected and washed with water and ether to give 0.70 g (70%) of the title compound: melting point of 160° C.-162° C.

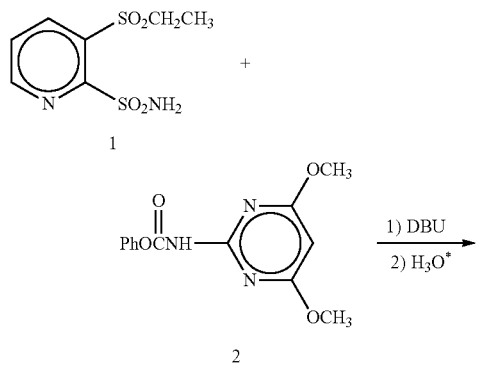

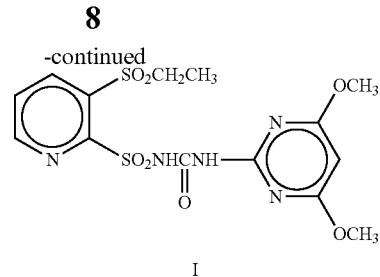

Figure 3:
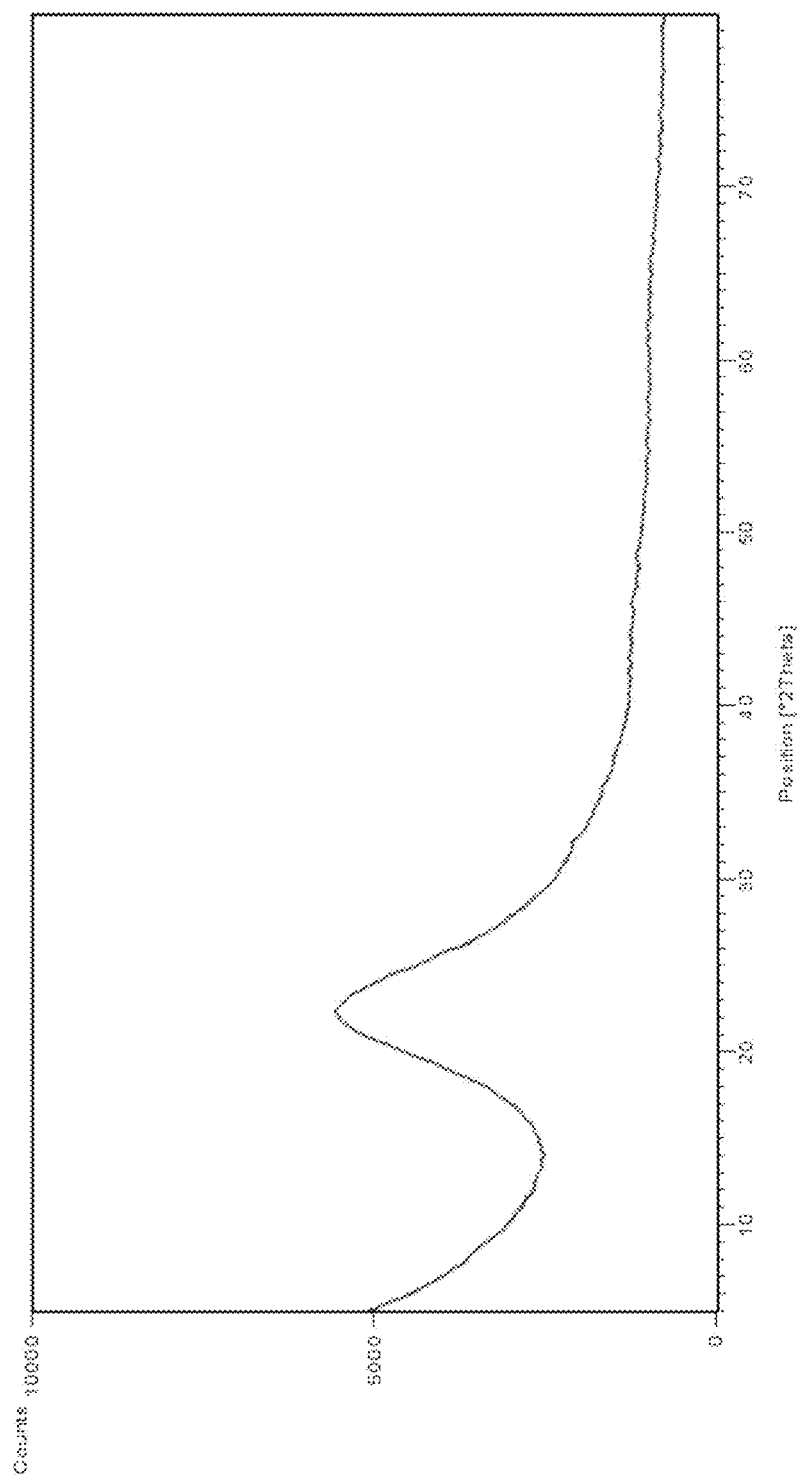
FIG. 3 is a X-ray powder diffraction pattern of a rimsulfuron.

As shown in FIG. 3, the X-ray powder diffraction pattern of the resulting rimsulfuron product has no significant signals, which indicates the rimsulfuron product prepared in accordance with the disclosure of EP0341011 A1 is amorphous.

Example 2

Preparation of the Crystal Form A of Rimsulfuron

Crystallization from Methanol 10 ml methanol was charged into the reactor to dissolve crude rimsulfuron prepared in example 1 under stirring. This process lasted for 2 hours under room temperature, and white solid precipitate appeared. The mixture was then cooled down to 0° C.-5° C. and maintained for 1 hour to allow complete crystallization. After that, the mixture was centrifuged. The filter cake was washed with methanol. The resulting solid was dried under high vacuum to give crystals of pure rimsulfuron technical (Purity: 98%).

The crystals were characterized as being of the crystal form A of rimsulfuron using both IR spectrometry and X-ray powder diffraction.

The IR spectrum of the crystal form A of rimsulfuron is set out in FIG. 2. The IR spectrum exhibits characteristic peaks at 3257.17 $cm^{-1}$ and 2943.91 $cm^{-1}$.

The crystal form A of rimsulfuron has the X-ray powder diffractogram shown in FIG. 1 with the reflexes listed in Table 1 below.

TABLE 1

| Crystal Form A | |
| --- | --- |
| 2θ (°) | d (Å) |
| 10.868 ± 0.2 | 8.14 ± 0.05 |
| 12.248 ± 0.2 | 7.23 ± 0.05 |
| 12.845 ± 0.2 | 6.89 ± 0.05 |
| 14.249 ± 0.2 | 6.22 ± 0.05 |
| 15.039 ± 0.2 | 6.12 ± 0.05 |
| 16.120 ± 0.2 | 5.50 ± 0.05 |
| 17.434 ± 0.2 | 5.09 ± 0.05 |
| 18.010 ± 0.2 | 4.93 ± 0.05 |
| 19.699 ± 0.2 | 4.51 ± 0.05 |
| 21.801 ± 0.2 | 4.08 ± 0.05 |
| 22.568 ± 0.2 | 3.94 ± 0.05 |
| 26.567 ± 0.2 | 3.56 ± 0.05 |

Example 3

Preparation of the Crystal Form A of Rimsulfuron

Crystallization from Ethanol 10 ml ethanol was charged into the reactor to dissolve crude rimsulfuron prepared in example 1 under stirring. This process lasted for 2 hours under room temperature, and white solid precipitate appeared. The mixture was then cooled down to 0° C.-5° C. and maintained for 1 hour to allow complete crystallization. After that, the mixture was centrifuged. The filter cake was washed with some ethanol. The resulting solid was dried under high vacuum to give crystals of pure rimsulfuron technical (Purity: 98%).

The crystals were characterized as being the crystal form A of rimsulfuron using IR spectrometry and X-ray powder diffraction as described in Example 2.

Example 4

Preparation of Oil Based Suspension Concentrate (OD) Formulation

All the components listed in Table 2 below were mixed uniformly and ground with a Dyno-Mill (manufactured by Willy A. Bachofen AG) to obtain an oil based suspension concentrate.

TABLE 2

| Ingredients | Weights % | | Function |
|---|---|---|---|
| Rimsulfuron, crystal form A, 98%, prepared in Example 2 | 40.8 | 0 | Active compound |
| Amorphous Rimsulfuron, prepared in Example 1 | 0 | 40.8 | Active compound |
| Sodium lignosulfonate (REAX ® 88B) | 22 | 22 | Dispersing agent |
| Alkylpolyvinylpyrrolidone | 20 | 20 | Thickening agent |
| Corn oil | Balance to 100% | Balance to 100% | Carrier |

Example 5

Preparation of Soluble Granules (SG)

All the components listed in Table 3 below were mixed, blended and milled in a high-speed rotary mill. Sufficient water was added to obtain an extrudable paste. The paste was extruded through a die or screen to form an extrudate. The wet extrudate was dried at 70° C. in a vacuum oven and then sifted through 0.71 mm-2 mm screens to obtain the product granules.

TABLE 3

| Ingredients | Weights % | | Function |
|---|---|---|---|
| Rimsulfuron, crystal form A, 98%, prepared in Example 2 | 25.51 | 0 | Active compound |
| Amorphous Rimsulfuron, prepared in Example 1 | 0 | 25.51 | Active compound |
| Lignosulfonic acid, sodium salt, (REAX ® 88B) | 15 | 15 | Dispersing agent |
| Naphthalenesulfonic acid, polymer with formaldehyde, sodium salt (TAMOL ® NN 8906) | 6 | 6 | Dispersing agent |
| Sodium acetate | 4 | 4 | Filler |
| Sodium carbonate | 4 | 4 | Filler |
| Non-ionic aqueous emulsion of Polydimethylsiloxanes | 1 | 1 | Antiform |
| Mannitol | Balance to 100% | Balance to 100% | carrier |

Example 6

Preparation of Water Dispersible Granules (WG)

All the components listed in Table 4 below were mixed, blended and milled in a high-speed rotary mill. Sufficient water were added to obtain an extrudable paste. The paste was extruded through a die or screen to form an extrudate. The wet extrudate was dried at 70° C. in a vacuum oven and then sifted through 0.71 mm-2 mm screens to obtain the product granules.

TABLE 4

| Ingredients | Weights % | | Function |
|---|---|---|---|
| Rimsulfuron, crystal form A, 98%, prepared in Example 2 | 25.51 | 0 | Active compound |
| Amorphous Rimsulfuron, prepared in Example 1 | 0 | 25.51 | Active compound |
| Alkyl naphthalene sulphonate, sodium salt (Akzo Nobel) | 2 | 2 | Wetting agent |
| Lignosulfonic acid, sodium salt, REAX ® 88B) | 15 | 15 | Dispersing agent |
| Naphthalenesulfonic acid, polymer with formaldehyde, sodium salt (TAMOL ® NN8906) | 6 | 6 | Dispersing agent |
| Sucrose | 10 | 10 | Filler |
| Non-ionic aqueous emulsion of Polydimethylsiloxanes | 1 | 1 | Antiform |
| Mannitol | Balance to 100% | Balance to 100% | Carrier |

Example 7

Determining Water Solubility

A stock pH 7 buffer solution was prepared by adding aqueous sodium hydroxide solution (0.1 M, 145 mL) to aqueous potassium dihydrogen phosphate solution (0.1 M, 250 mL), and then adding sufficient distilled water to adjust the final volume to 500 mL. At least 1 time and up to about 5 times the amount of rimsulfruon needed for saturation was added to a mixing vessel containing stock buffer solution at the test temperature (e.g., 20° C.). The mixture was magnetically stirred in the dark while being maintained at the test temperature. Samples were periodically removed for analysis. The samples were centrifuged using a high speed, temperature-controlled centrifuge at the test temperature for about 20 minutes at ≥12000 G to remove suspended particles. An aliquot of each supernatant was taken for analysis.

The concentration of rimsulfuron in the supernatant was determined by a high pressure liquid chromatography (HPLC) with a reversed phase chromatography column and UV detection. The method should include development of best-fit calibration curves based on at least three standards using linear regression analysis Samples were successively withdrawn from the mixing vessel and analyzed until three successive samples show little or no variation in concentration. The test is preferably replicated to ensure accuracy.

TABLE 5

| Sample | Formulation | Original concentration, % | Concentration measured by HPLC after treatment, % | Solubility |
|---|---|---|---|---|
| Rimsulfuron, crystal form A, 98%, prepared in Example 2 | OD | 40 | 35 | 88% |

TABLE 5-continued

| Sample | Formulation | Original concentration, % | Concentration measured by HPLC after treatment, % | Solubility |
|---|---|---|---|---|
| Amorphous Rimsulfuron, prepared in Example 1 | OD | 40 | 14 | 35% |
| Rimsulfuron, crystal form A, 98%, prepared in Example 2 | SG | 25 | 24.9 | 99.6% |
| Amorphous Rimsulfuron, prepared in Example 1 | SG | 25 | 15 | 60% |
| Rimsulfuron, crystal form A, 98%, prepared in Example 2 | WG | 25 | 23 | 92% |
| Amorphous Rimsulfuron, prepared in Example 1 | WG | 25 | 12 | 48% |

Example 8

Cleanout Test

The cleanout test was conducted by dispersing in water a sample to produce a concentration that is normally used when applying the herbicide: 25% rimsulfuron. The sample was added to tap water (300 mL) in a 400 mL beaker and magnetically stirred for 2 minutes. The mixture was then stirred for 2 minutes, whereupon the resulting dispersion was dispensed in three 100 mL aliquots to 4-oz (118 mL) polyethylene bottles. The bottles were capped, inverted twice and allowed to stand overnight.

After standing overnight, each individual bottle was inverted twice and the liquid contents were then poured out. Tap water (10 mL) was added and the bottle was inverted until all sediment was re-suspended, whereupon the contents were poured out. Tap water (100 mL) was added and the bottle was inverted twice and then allowed to stand undisturbed for 10 minutes. The bottle was inverted twice more and the contents were poured out. Acetonitrile (10 mL) was added to the bottle to extract any remaining material. The acetonitrile solution was analyzed by reversed-phase liquid chromatography with UV detection. The cleanout rating (the concentration of rimsulfuron herbicide in the acetonitrile solution) is reported in % in Table 6 below. Lower cleanout ratings indicate more effective cleanout compared to higher ratings.

TABLE 6

| Sample | Formulation | Cleanout rating, % |
|---|---|---|
| Rimsulfuron, crystal form A, 98%, prepared in Example 2 | OD | 5 |
| Amorphous Rimsulfuron, prepared in Example 1 | OD | 26 |
| Rimsulfuron, crystal form A, 98%, prepared in Example 2 | SG | 0.1 |
| Amorphous Rimsulfuron, prepared in Example 1 | SG | 10 |
| Rimsulfuron, crystal form A, 98%, prepared in Example 2 | WG | 2 |
| Amorphous Rimsulfuron, prepared in Example 1 | WG | 13 |

The results in Table 6 demonstrate that the crystal form A of rimsulfuron exhibited markedly superior cleanout properties than the known amorphous rimsulfuron product.

The invention claimed is:

1. A crystal form A of rimsulfuron, exhibiting each of the following reflexes in an X-ray powder diffractogram recorded using Cu—Kα radiation at 25° C.:

$$2\theta=10.868\pm0.2 \quad (1)$$

$$2\theta=12.248\pm0.2 \quad (2)$$

$$2\theta=12.845\pm0.2 \quad (3)$$

$$2\theta=14.249\pm0.2 \quad (4)$$

$$2\theta=15.039\pm0.2 \quad (5)$$

$$2\theta=16.120\pm0.2 \quad (6)$$

$$2\theta=17.434\pm0.2 \quad (7)$$

$$2\theta=18.010\pm0.2 \quad (8)$$

$$2\theta=19.699\pm0.2 \quad (9)$$

$$2\theta=21.801\pm0.2 \quad (10)$$

$$2\theta=22.568\pm0.2 \quad (11)$$

$$2\theta=26.567\pm0.2 \quad (12).$$

2. The crystal form A of rimsulfuron according to claim 1, exhibiting IR spectrum with the characteristic bands at 3257.17 $cm^{-1}$ and 2943.91 $cm^{-1}$.

3. A composition comprising the crystal form A of rimsulfuron according to claim 1 and at least one auxiliary.

4. The composition according to claim 3, in the form of a suspension concentrate (SC), an oil-based suspension concentrate (OD), water-soluble granules (SG), a dispersible concentrate (DC), an emulsifiable concentrate (EC), an emulsion seed dressing, a suspension seed dressing, granules (GR), microgranules (MG), a suspoemulsion (SE) or water-dispersible granules (WG).

5. The composition according to claim 3, wherein the auxiliary is selected from one or more of a solvent, a diluent, a wetting agent, a dispersant, and a thickener.

6. The composition according to claim 3, which comprises crystal form A of rimsulfuron in an amount of less than 75% by weight.

7. A composition comprising crystal form A of rimsulfuron according to claim 1.

8. A process for the preparation of a crystal form A of rimsulfuron according to claim 1, the process comprising:
  i) preparing a solution of an amorphous rimsulfuron in a solvent, wherein the solvent is methanol and/or ethanol;
  ii) effecting crystallization of rimsulfuron from the solution to obtain a solid precipitate; and
  iii) isolating the solid precipitate.

9. A method for controlling unwanted plant growth, comprising applying to the plant, plant part, or surroundings of the plant, a herbicidally effective amount of crystal form A of rimsulfuron according to claim 1.

* * * * *